United States Patent
Barton et al.

(10) Patent No.: US 6,777,405 B2
(45) Date of Patent: Aug. 17, 2004

(54) DETECTION AND TREATMENT OF DUPLEX POLYNUCLEOTIDE DAMAGE

(75) Inventors: Jacqueline K. Barton, San Marino, CA (US); Brian A. Jackson, Pasadena, CA (US); Brian P. Hudson, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/235,433

(22) Filed: Sep. 3, 2002

(65) Prior Publication Data

US 2003/0018020 A1 Jan. 23, 2003

Related U.S. Application Data

(62) Division of application No. 09/448,325, filed on Nov. 23, 1999, now Pat. No. 6,444,661, which is a division of application No. 09/132,357, filed on Aug. 11, 1998, now Pat. No. 6,031,098.
(60) Provisional application No. 60/055,691, filed on Aug. 11, 1997.

(51) Int. Cl.[7] ........................ A61K 31/555; A61K 31/44; A61K 31/41
(52) U.S. Cl. ........................ 514/185; 514/187; 514/188; 514/288; 514/360
(58) Field of Search ................ 514/185, 187, 514/188, 288, 360; 546/2, 88; 856/137

(56) References Cited

U.S. PATENT DOCUMENTS

| | | | |
|---|---|---|---|
| 5,157,032 A | * | 10/1992 | Barton .................. 514/185 |
| 6,063,573 A | | 5/2000 | Kayyem |
| 6,071,699 A | | 6/2000 | Meade et al. |
| 6,087,100 A | | 7/2000 | Meade et al. |
| 6,090,933 A | | 7/2000 | Kayyem et al. |
| 6,096,273 A | | 8/2000 | Kayyem et al. |

* cited by examiner

*Primary Examiner*—Shaojia Anna Jiang
(74) *Attorney, Agent, or Firm*—Gray Cary Ware & Freidenrich, LLP

(57) ABSTRACT

Duplex polynucleotides containing damage or errors are detected with hindered intercalating compounds which are capable of intercalating only in the presence of such damage or error. Conditions characterized by the presence of polynucleotide errors or damage are treated with such compounds that are capable of catalyzing polynucleotide cleavage with light. Suitable compound include compounds of the formula:

$$Rh(R_1)(R_2)(R_3)^{3+}$$

where $R_1$ and $R_2$ are each independently aryl, heteroaryl, substituted aryl or substituted heteroaryl of 1 to 5 rings, and $R_3$ is a group of the formula

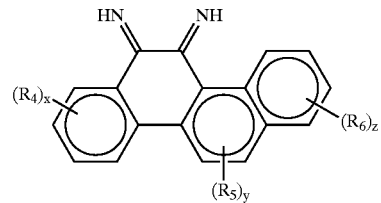

where x and z are each independently an integer from 1 to 4 and y is an integer from 1 to 2, and $R_4$, $R_5$, and $R_6$ are each independently H—, halo, HO—, $H_2N$—, CN—, $O_2N$—, HS—, $O_3S$—, $O_3SO$—, —COOH, —$CONH_2$, R, RO—, RNH—, $R_aR_bN$—, $RO_3S$—, $RO_3SO$—, —COOR, —CONHR, or —$CONR_aR_b$, where R, $R_a$ and $R_b$ are each independently lower alkyl, cycloalkyl, lower alkenyl, lower alkynyl, or phenyl, or two $R_4$, $R_5$, or $R_6$ together form a fused aryl ring.

5 Claims, 2 Drawing Sheets

SEQUENCE LISTING

<160> NUMBER OF SEQ ID NOS: 3

<210> SEQ ID NO 1
<211> LENGTH: 17
<212> TYPE: DNA
<213> ORGANISM: Artificial sequence
<220> FEATURE:
<223> OTHER INFORMATION: OLIGONUCLEOTIDE SYNTHESIZED USING PHOSPHORAMIDITE CHEMISTRY
<220> FEATURE:
<221> NAME/KEY: misc_feature
<222> LOCATION: (9)..(9)

```
<223> OTHER INFORMATION: n is either g, c, t, or a

<400> SEQUENCE: 1
gcggagtcnt gcatgtg                                                   17

<210> SEQ ID NO 2
<211> LENGTH: 17
<212> TYPE: DNA
<213> ORGANISM: Artificial sequence
<220> FEATURE:
<223> OTHER INFORMATION: OLIGONUCLEOTIDE SYNTHESIZED USING
      PHOSPHORAMIDITE CHEMISTRY
<220> FEATURE:
<221> NAME/KEY: misc_feature
<222> LOCATION: (9)..(9)
<223> OTHER INFORMATION: n is either a, g, t, or c

<400> SEQUENCE: 2
cacatgcang actccgc                                                   17

<210> SEQ ID NO 3
<211> LENGTH: 35
<212> TYPE: DNA
<213> ORGANISM: Artificial sequence
<220> FEATURE:
<223> OTHER INFORMATION: OLIGONUCLEOTIDE SYNTHESIZED USING
      PHOSPHORAMIDITE CHEMISTRY

<400> SEQUENCE: 3
catcatgtcc tgccctttt gggcacgaca tgatg                                35
```

DETECTION AND TREATMENT OF DUPLEX POLYNUCLEOTIDE DAMAGE

CROSS REFERENCE TO RELATED APPLICATIONS

This application is a divisional of U.S. application Ser. No. 09/448,325, filed Nov. 23, 1999, now U.S. Pat. No. 6,444,661; which is a divisional of U.S. application Ser. No. 09/132,357, filed Aug. 11, 1998, now U.S. Pat. No. 6,031,098; which claims priority under 35 U.S.C. §119(e) from U.S. Provisional Application Serial No. 60/055,691, filed Aug. 11, 1997, all of which are incorporated herein by reference in its entirety.

STATEMENT AS TO FEDERALLY SPONSORED RESEARCH

This invention resulted from research funded in whole or part by the National Institutes of Health, Grant No. GM33309. The Federal Government may have certain rights in this patent.

FIELD OF THE INVENTION

This invention relates generally to the fields of inorganic and nucleotide chemistry. More specifically, the invention relates to compounds and methods for detecting base pair mismatches in oligonucleotides.

BACKGROUND OF THE INVENTION

DNA base mismatches arise during the course of genetic recombination and replication as a consequence of enzymatic errors or DNA damage. In the cell, complex systems exist to recognize, remove and repair these mistakes to preserve the integrity of the genetic code. Furthermore, in certain diseases, particularly cancer, these repair systems fail and mismatches persist in a diseased cell's DNA. The design of molecules and systems site specific recognize mismatches in DNA is an attractive experimental goal both for genetic screening and the design of new chemotherapeutics. Existing strategies include assays using isolated mismatch recognition proteins, hybridization of oligonucleotide-fluorescent probe conjugates, electrophoretic/DNA chip methods, and differential chemical cleavage with reagents assaying for base accessability either in solution or the solid phase. None of these methods are ideal for detection of mismatches in the laboratory, and no strategies exist for using the presence of base mismatches as a way of selective treating disease.

SUMMARY OF THE INVENTION

The present invention is based on the discovery of a new claim of compounds. These compounds intercalate between bases in a duplex polynucleotide, but only where the bases are not fully complementary, for example, where there is a base mismatch. The compounds are sufficiently hindered that intercalation between bases in fully complementary duplexes does not occur to a significant degree. These mismatch intercalators are useful for detecting DNA and RNA defects, for diagnosing disorders characterized by the presence or increase in DNA and/or RNA defects, and for treating such disorders.

A new class of compounds including $Rh(R_1)(R_2)(R_3)^{3+}$ and derivatives thereof is here described. The compound intercalates only between nucleotide bases in the presence of a base mismatch, and is useful for detecting single base mismatches. Further, the compound is capable of catalyzing photolytic cleavage of nucleic acids at relatively long wavelengths, and under normal sunlight.

One aspect of the invention is a compound of the formula $Rh(R_1)(R_2)(R_3)^{3+}$ and derivatives thereof.

Another aspect of the invention is a composition comprising two complementary oligonucleotide strands having a base mismatch, and a compound of the invention.

Another aspect of the invention is a method for determining the presence of a base mismatch in an oligonucleotide, by adding a compound of the invention to a double-stranded oligonucleotide, subjecting the complex to photocleavage conditions, and determining the presence or absence of cleavage products.

Another aspect of the invention is a method for diagnosing a disorder characterized by the presence or increased presence of DNA and/or RNA disorders (for example base pair mismatches), by administering a mismatch intercalator to a cell suspecting of having such a disorder, and determining whether intercalation occurs.

Another aspect of the invention is a method for treating a disorder characterized by the presence or increased presence of DNA and/or RNA disorders (for example base pair mismatches), by administering a compound of the invention to a cell having such disorder, and optionally treating said cell with sufficient light to cause polynucleotide cleavage.

One object of the invention is to provide a method for detecting nucleic acid base mismatches in duplexes.

Another object of the invention is to provide compounds useful for labeling or indicating base mismatches. Another object of the invention is to provide a compound capable of catalyzing cleavage of a duplex having a base mismatch.

Another object of the invention is to provide a method for diagnosing and/or treating a disorder characterized by the presence of base mismatches in nucleic acid duplexes.

Another object of the invention is to provide compounds useful for diagnosing and/or treating disorders characterized by the presence of base mismatches in nucleic acid duplexes.

Another object of the invention is to provide a method for screening agents for their ability to damage nucleic acid duplexes.

DETAILED DESCRIPTION OF THE INVENTION

Definitions

Figure 1:
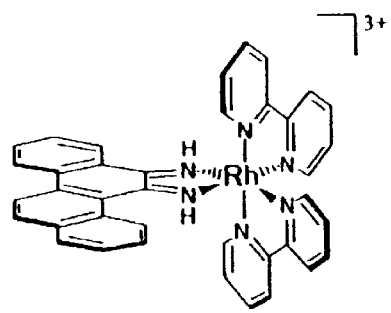
FIG. 1 shows the results of photocleaving DNA duplexes having a single base pair mismatch using the compound of the invention.
Figure 1:
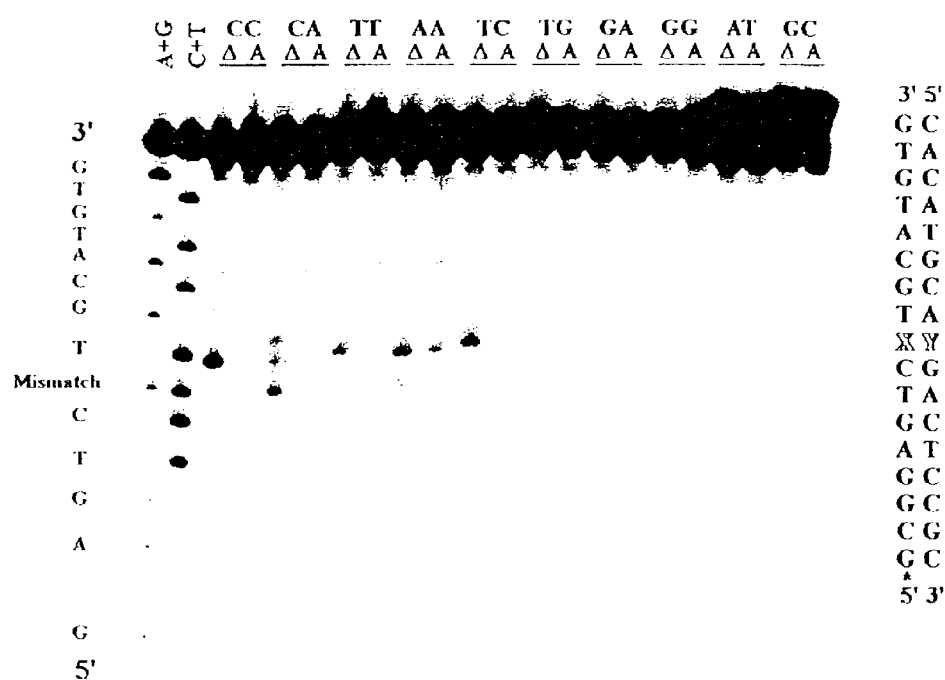

The term "hindered intercalating compound" or "hindered intercalating agent" as used herein refers to a compound that is not capable of substantially intercalating between the bases of a normal duplex polynucleotide, but is capable of intercalating between the bases of a duplex polynucleotide having error and/or damage. A labeled agent is a hindered intercalating agent bearing a detectable label, as defined below. A "cleaving" agent is a hindered intercalating agent that is capable of cleaving or catalyzing the cleavage of a polynucleotide duplex in which it is intercalated. A "photo-cleaving" compound or agent is a hindered intercalating agent capable of catalyzing photolysis of a polynucleotide in which it is intercalated.

The terms "damage" and "error" as used herein refer to a departure from the "normal" or ideal structure of a polynucleotide duplex. In the "ideal" structure, all bases are paired with complementary bases, and no nicks, breaks, or gaps occur in the backbones. "Error" describes the condition in which a base is paired with a non-complementary base, or a base is absent from a position (abasic), or a gap exists in the sequence of one strand (e.g., the strands have different numbers of bases, and the unpaired location does not occur at the end of the strand). "Error" includes simple base pair mismatches, for example in which a denatured DNA sample is hybridized with a substantially (but not completely) complementary oligonucleotide probe: the probe and target can depart from complentarity by one or more bases. "Damage" describes the condition in which the conformation of the duplex is perturbed, for example by a nick in the backbone, T-T dimerization, and the like.

In humans, each cell division requires the replication of approximately six billion bases of DNA. Most errors are detected and corrected by DNA repair enzymes. However, DNA repair enzymes are inactive or inefficient in some forms of cancer: these cancers can be diagnosed by the presence of higher than normal numbers of base mismatches per cell. A "condition" or "disorder" characterized by polynucleotide damage or error is a pathological state that can be distinguished from a normal state by the presence of an increased level, rate, or concentration of damage and/or errors in polynucleotide duplexes. The increase in polynucleotide damage and/or error can be determined with respect to a control, or with respect to a known or previously measured rate established for "normal" individuals.

The term "compound of formula 1" and "compound of the invention" refers a compound of the formula $Rh(R_1)(R_2)(R_3)^{3+}$, wherein $R_1$ and $R_2$ are each independently aryl, heteroaryl, substituted aryl or substituted heteroaryl of 1 to 5 rings, and $R_3$ is a group of the formula

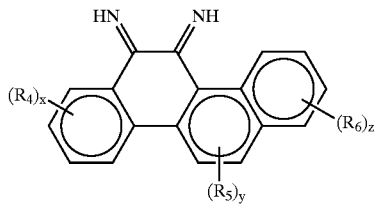

where x and z are each independently an integer from 1 to 4 and y is an integer from 1 to 2, and $R_4$, $R_5$, and $R_6$ are each independently H—, halo, HO—, $H_2N$—, CN—, $O_2N$—, HS—, O—, S—, O—, SO—, —COOH, —$CONH_2$, R, RO—, RNH—, $R_aR_bN$—, $RO_3S$—, $RO_3SO$—, —COOR, —CONHR, or —$CONR_aR_b$, where R, $R_a$ and $R_b$ are each independently lower alkyl, cycloalkyl, lower alkenyl, lower alkynyl, or phenyl, or two $R_4$ together form a fused aryl ring.

The term "bpy" refers to 2,2'-bipyridyl.

The term "bpy" refers to 4-butyric acid-4-methyl-bipyridyl.

The term "phen" refers to 1,10-phenanthroline.

The term "chrysi" indicates the bidentate ligand 5,6-chrysene quinone diimine:

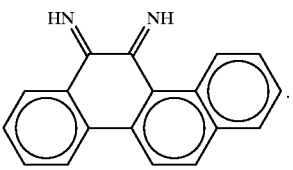

The prefixes "Λ" and "Δ" refer to different enantiomers of the compound of the invention.

The term "aryl" as used herein refers to a moiety having one to about five rings, of which at least half are aromatic. Exemplary aryl groups include, without limitation, phenyl, naphthyl, biphenyl, terphenyl, 2-phenyl-naphthyl, anthryl, phenanthryl, fluorenyl, indanyl, cholanthrenyl, acephenanthrenyl, and the like.

The term "heteroaryl" as used herein refers to an aryl moiety having one or more heteroatoms, preferably no more than about three heteroatoms per ring. Heteroatoms can include, for example, oxygen, sulfur, nitrogen, boron, and phosphorus. Exemplary heteroaryl groups include pyridyl, pyrazinyl, indolyl, cinnolinyl, carbazolyl, acridinyl, quinazolinyl, purinyl, benzofuranyl, benzothienyl, quinolyl, phenothiazinyl, and the like.

The terms "substituted aryl" and "substituted heteroaryl" refer to aryl and heteroaryl moieties as described above, further having at least one substituent. Substituted aryl and substituted heteroaryl preferably have no more than about four substituents per ring, preferably no more than three per ring. Suitable substituents include, without limitation, halo. HO—, $H_2N$—, CN—, $O_2N$—, HS—, $O_3S$—, $O_3SO$—, —COOH, —$CONH_2$, R, RO—, RNH—, $R_aR_bN$—, $RO_3S$—, $RO_3SO$—, —COOR, —CONHR, and —$CONR_aR_b$, where R, $R_a$ and $R_b$ are each independently lower alkyl, cycloalkyl, lower alkenyl, lower alkynyl, or phenyl.

The term "halo" refers to fluoro, chloro, bromo, and iodo.

The term "alkyl" refers to a fully saturated branched or unbranched hydrocarbon moiety. The term "lower alkyl" refers to an alkyl moiety having from one to about six carbon atoms. Suitable lower alkyl radicals include, without limitation, methyl, ethyl, propyl, isopropyl, butyl, but-2-yl, hexyl, and the like.

The term "cycloalkyl" refers to a saturated hydrocarbon radical having one to three rings, and containing from three to about nine carbon atoms in the ring structure. Suitable cycloalkyl moieties include, without limitation, cyclopropyl, cyclobutyl, cyclopentyl, cyclohexyl, 3-methylcyclohexyl, bicyclooctyl, norbornyl, and the like.

The term "alkenyl" refers to a straight, branched, or cyclic hydrocarbon radical that includes a double bond, but does not include a triple bond. The term "lower alkenyl" refers to an alkenyl radical having from two to about six carbon atoms. Suitable lower alkenyl moieties include, without limitation, vinyl, allyl, 2-butenyl, cyclohexenyl, and the like.

The term "alkynyl" refers to a straight, branched, or cyclic hydrocarbon radical that includes a triple bond. The term "lower alkynyl" refers to an alkynyl radical having from two to about six carbon atoms. Suitable lower alkynyl moieties include, without limitation, acetenyl, 2-propynyl, 3-butynyl, and the like.

The term "effective amount" refers to the amount of compound necessary to cause cleavage of an oligonucleotide duplex having a base mismatch when subjected to light of sufficient energy. The minimum effective amount can vary depending on reaction conditions and the identity of the bases involved in the mismatch, but in general will range from a ratio of about 100:1 to about 1:1 nucleotide:compound. The effective amount for a particular application can vary with the conditions employed, but can be determined using only routine experimentation.

The term "label" as used herein refers to a moiety that is detectable or can be manipulated to provide a detectable signal. Suitable detectable labels include, without limitation, radioactive atoms such as $^3$H, $^{14}$C, and the like, fluorophores, chromophores, electron-dense reagents, isotopic labels, enzymes capable of catalyzing signal reactions such as chromogenic, luminescent, and fluorescent reactions, binding ligands, cleaving molecules, and the like. "Binding ligands" are moieties capable of binding a labeled compound or a solid support; for example, a detectable label can comprise a moiety capable of binding a polynucleotide duplex to a solid support, where the polynucleotide can be detected directly, for example by PCR or hybridization assays. Alternatively, a binding ligand can bind to another compound which bears a detectable label, for example an enzyme-labeled antibody. Cleaving molecules are capable or cleaving, or catalyzing the cleavage of, polynucleotides: this can serve as a label by, for example, releasing one end of a duplex polynucleotide from a surface-bound complex. One can detect the released ends, for example by end-labeling the strands prior to cleavage, or can detect the newly cleaved end bound to the support, for example where the duplexes are end-protected prior to cleavage, and subject to enzymatic degradation in the absence of the end protecting group.

The term "cleavage conditions" refers to reaction conditions sufficient to cause cleavage of an oligonucleotide duplex having a base mismatch in the presence of a effective amount of a compound of the invention. "Photocleavage conditions" are those conditions sufficient to cause photolysis of a polynucleotide in the presence of an effective amount of photocleaving compound or agent.

The term "mutagenic agent" refers to a physical, chemical, or biological agent capable of causing DNA and/or RNA damage or errors. Examples of known mutagenic agents include, without limitation, ionizing radiation, ultraviolet light, 2-aminopurine, 5-bromouracil, hydroxylamine, nitrous acid, ethyl ethane sulfonate, nitrosamines, nitrogen mustard, acridine, proflavin, and the like.

The term "stringent conditions" refers to polynucleotide hybridization conditions (generally a combination of temperature, concentration, and denaturing agent) under which a probe oligonucleotide will bind to a target polynucleotide only if completely complementary. "Non-stringent conditions" are hybridization conditions which tolerate the presence of one or more base mismatches, i.e., where substantially complementary polynucleotides will hybridize. Substantially complementary polynucleotides can differ from exact complementarity in 5% or more of the base positions, or can contain a few as a single base mismatch.

General Method

One aspect of the invention is based on the discovery that one can prepare intercalating compounds that are too hindered to intercalate between the bases of a "normal" polynucleotide duplex, but can intercalate between the bases of a duplex in the presence of damage or error. Such compounds are useful for indicating the presence of polynucleotide damage or error, for diagnosing conditions characterized by polynucleotide damage or error, for separating or isolating damaged or erroneous polynucleotides, and for treating conditions characterized by polynucleotide damage or error.

One method of the invention is a method for determining the existence of a difference between a target polynucleotide and a probe oligonucleotide. Previous methods for detecting a base mismatch between a probe and a target relied on sensitive adjustment of hybridization conditions (e.g., temperature and concentration), such that hybridization occurred only where the probe and target were completely complementary, and not otherwise ("stringent conditions"). Using hindered intercalating compounds, however, one can directly label polynucleotide duplexes having a base mismatch, and thus directly detect lack of full complementarity between a probe and a target under non-stringent conditions. Thus, in one embodiment of the invention, a sample containing a target polynucleotide is provided, contacted with a probe oligonucleotide under non-stringent conditions, contacted with a labeled hindered intercalating compound, and the product duplex nucleic acids examined for the presence of label. This method can be used, for example, to diagnose hereditary differences and/or the presence of genetic defects, to distinguish between different strains of pathogenic organisms, to establish paternity, to distinguish between a subject's DNA and DNA found in a forensic sample, amongst other uses. The sample/target polynucleotide can be provided in single strand or double strand form, but is preferably denatured prior to hybridization with the probe oligonucleotide. The probe oligonucleotide can be as short as about 8–10 bases, up to a length of several thousand bases: the probe can be as long or longer than the target polynucleotide.

The method can be facilitated by binding the target, probe, or intercalating compound to a solid support, to simplify washing and purification. Thus, for example, one can provide a solid support (such as a microwell format plate, dipstick, membrane or other surface) having a probe immobilized on the surface. If desired, the complementary portion of the probe can be attached to a spacer, to permit the probe to interact with the target polynucleotide away from the support surface. The sample polynucleotide is added or spotted on the support, and allowed to hybridize with the probe under non-stringent conditions. The surface is then washed to remove any non-hybridized material, contacted with a hindered intercalating agent, and washed again to remove any non-bound compound. If the probe and target are exactly complementary, the hindered intercalating compound does not bind, and no signal appears. If at least one base mismatch is present, the compound intercalates and provides a detectable signal. One can use a cleaving agent, for example a photocleaving agent of the invention, and detect the presence of base mismatches by exposing the bound duplexes to cleaving conditions, eluting any released oligonucleotides, and sizing the resulting fragments, for example by polyacrylamide gel electrophoresis (PAGE). Knowledge of the probe sequence and the size of the released fragment permits one to determine the position of the base mismatch.

Another method of the invention is the method of detecting DNA damage or errors existing in a cell, by contacting the DNA with a labeled hindered intercalating compound, and determining whether or not the compound binds to DNA in the cell. This method is useful for detecting or diagnosing conditions characterized by increased DNA damage and/or errors, such as congenital defects in DNA repair or error-correction enzymes, cancer, and the like. Further, the method is useful for determining and quantifying mutagenic effects of other compounds on a given host cell, for example, by determining the "natural" error/damage rate for a host cell population, exposing a population of host cells to a potential mutagenic agent, contacting the cell with a labeled hindered intercalating compound, and determining whether or not the compound binds to DNA in the cell.

Intracellular labeling can be detected by standard means, for example, by detecting fluorescence of a labeled intercalating compound. Alternatively, one can employ a cleaving compound, and effect cleavage of any intercalated DNA. The cell can then be lysed, and the resulting DNA fragments sized (and compared to controls).

Hindered intercalating compounds can be prepared starting from known intercalating compounds and principles, by adding bulky or large groups to the compound until it is incapable of intercalating in normal polynucleotide duplexes. One can screen for such compounds by providing a library of potential hindered intercalating compounds, and providing a substrate with a plurality of normal duplexes and a plurality of damaged or erroneous duplexes (e.g., duplexes having one or more base mismatches, preferably of several different sequences). The compounds are first applied to the normal duplexes, and all compounds that intercalate are eliminated. The remainder are then applied to the damaged duplexes, and the compounds that intercalate are separated and/or identified to provide hindered intercalating compounds. This set of compounds can be further screened for photolytic activity by exposing the compound-duplex complexes to light of sufficient energy for varying periods of time, and identifying any compounds released by photolysis.

Hindered intercalating compounds can be labeled by a variety of methods known in the art. For example, the compounds can be prepared incorporating radioactive atoms or electron-dense reagents. Alternatively, the compounds can be conjugated with fluorophores, chromophores, spin labels, enzymes, antibodies or ligands, and the like. Further, some hindered intercalating compounds are intrinsically colored or fluorescent, and are thus "self-labeled." Additionally, some hindered intercalating compounds exhibit a shift in peak fluorescence or color when intercalated (as compared with their solution state). Such compounds can be used in assays for detecting damaged or error-containing polynucleotide duplexes by adding the compound and monitoring the sample for appearance of the color or fluorescence peak that indicates an intercalated hindered compound.

Active hindered intercalating compounds can be used to diagnose and treat conditions characterized by the presence of a substantial number of polynucleotide errors or damaged locations. Diagnosis is accomplished by contacting a nucleic acid sample with a labeled hindered intercalating compound, whether by introducing the compound into a cell or by extracting the nucleic acids from a cell. The product is examined for the number or quantity of errors or damage present, and is compared to a control sample or to an established standard or threshold. For example, one can obtain a biopsy, lysed the cells and extract the nucleic acids, add a labeled compound to the nucleic acids, and examine the sample for the presence of bound label: bound label indicates the presence of duplex damage or errors, while the absence of bound label, or a quantity of bound label comparable to the noise level, indicates normal duplexes.

Conditions or disorders characterized by damaged or erroneous duplexes in localized areas, such as cancers, can be treated using active hindered intercalating compounds. Upon entry into a cell, the compounds intercalate at damaged or mismatched sites in the DNA. In some cases, the presence of a compound intercalated between the basis is sufficient to trigger cellular activity, up to and including apoptosis. Normal DNA is not affected. If binding is not sufficient, the cells are then exposed to sufficient illumination to photolyse the DNA where compounds are intercalated. DNA photolysis triggers various cellular mechanisms, including apoptosis, thus eliminated affected cells. The suitability of compounds of the invention for such uses can be assayed using the procedures provided in the examples below, or further by conducting photocleavage titration using transformed cell lines or clinical tumor samples instead of naked DNA oligonucleotides.

Compounds of formula 1, $Rh(R_1)(R_2)(R_3)^{3+}$, are prepared by the methods set forth in the examples below.

Hindered intercalating compounds can be administered orally or parenterally, for example by injection, inhalation, transdermally, and the like, and can be administered in vivo or ex vivo. For example, one can use compounds of the invention to purge bone marrow of tumor cells prior to reintroducing the marrow into a patient (e.g., after radiotherapy). The compounds can be administered systemically or locally, for example via indwelling catheter, controlled- or sustained-release implant, minipump, and the like. Alternatively, the compounds can be formulated as an aerosol, and administered to the lungs and trachea.

The compounds can be formulated in a liquid dosage form such as, for example, liquids, suspensions or the like, preferably in unit dosage forms suitable for single administration of precise dosages. Liquid dosages may be administered by injection or infusion, as nose drops or as an aerosol. Alternatively, the active compound can be prepared as a creme or an ointment composition and applied topically. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., *Biomaterials* (1981) 2:201). Natural polymers, such as gelatin and cellulose slowly dissolve in a matter of minutes to hours while silicone remains intact for a period of months. The compositions will include a conventional pharmaceutical carrier or excipient, one or more of the active compound(s). In addition, the compositions may include other medicinal agents, pharmaceutical agents, carriers, adjuvants, etc.

The amount of compound administered will of course, be dependent on the subject being treated, the severity of the affliction, the manner of administration, the frequency of administration, and the judgment of the prescribing physician. Suitable concentrations can be determine by one of ordinary skill in the art, using only routine experimentation. The frequency of administration is desirably in the range of an hourly dose to a monthly dose. preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. The preparation can additionally contain compounds that facilitate entry of the nucleic acid of interest into the inner ear cells such as Lipofectin, permeability-enhancing agents (e.g., detergents), or other transformation-enhancing agents. Actual methods of preparing such dosage forms are known, or will be apparent, to those skilled in this art; for example, see *Remington's Pharmaceutical Sciences*, Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, eleostearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates orbita, e.g., those sold under the trademarks "Arlacel C" (sorbitan sesquioleate), "Span 80" (sorbitan monoleate) and "Span 85" (sorbitan trioleate). The surfactant may constitute 0.1=20% by weight of the composition, preferably 0.25-5%.

The balance of the composition is ordinarily propellant. Liquefied propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

EXAMPLES

The following examples are provided as a guide for those skilled in the art, and are not to be construed as limiting the invention in any way. All products are used according to manufacturer's instructions, and experiments are conducted under standard conditions, unless otherwise specified.

The NMR studies ($^1$H and $^{13}$C NMR, 2D-COSY, $^1$H$^{13}$C-HETCOR and decoupling experiments) were performed on a General Electric QE Plus 300 MHZ instrument using solvent as the internal standard. Electronic spectra were measured on a Varian Cary 2200 and a Beckmann DU 7400 UV/vis spectrophotometer. Mass spectral data were collected at the mass spectra facilities of the University of California, Riverside, Calif. (FAB and electro-spray), and at the Macromolecular Resources Center of Colorado State University, Department of Biochemistry, Fort Collins, Colo. (MALDI and electrospray). CD spectra were measured on a Jasco J-500A spectropolarimeter. High-performance liquid chromatography (HPLC) was carried out with a HP 1050 system on a Rainin Microsorb-MV $C_{18}$ 100 Å column (1.0 mL/min liquid phase, linear gradient over 45 min from 0.1% trifluoroacetic acid in water to 100% acetonitrile). Thin-layer chromatography was conducted on silica gel IB-F plates (J. T. Baker).

Unless otherwise specified, commercial chemicals were used as supplied. $RhCl_3 \cdot 2H_2O$ was obtained from Johnson & Matthey or Aldrich, 9,10-phenanthrenequinone, (+)-KSb-tartrate, triflic acid, and Sephadex cation and anion exchange resins were from Aldrich, $[Rh(NH_3)_5Cl]Cl_2$ was from Pfaltz+Bauer, MeCN of spectroscopic quality was from Merck, and chrysene was from Acros Chemicals. $d_8$-2,2'-Bipyridine was kindly donated by P. Belser and A. von Zelewsky, Fribourg University, Fribourg, Switzerland. 5,6-Chrysene-quinone (Greabe, V. C., and Honigsberger, F., *Justus Liebigs Ann. Chem.* (1900) 311:257–65) and [Rh$(NH_3)_6$]$(CF_3SO_3)_3$ (Curtis, N. J., et al., 1983, *J. Am. Chem. Soc.* (1983) 105:534–53) were prepared according to published procedures.

Example 1
Synthesis of Rhodium Amine Intermediates (A) Synthesis and Characterization. rac-[RH(phen)$_2$(NH$_3$)$_2$](PF$_6$)$_3$.

Bis(amine)bis(phenanthroline)rhodium(III) was prepared as described in the literature (Gidney, P. M., et al., 1972, *J Chem. Soc., Dalton Trans.* 2621–28) with the following modifications: The chloride ligands of [Rh(phen)$_2$Cl$_2$]Cl were substituted by stirring in neat triflic acid overnight (Dixon, N. E., et al., 1990, *Inorg. Synth.* 28:71–76). The brownish solution was carefully introduced into chilled diethyl ether. The beige precipitate was separated either by centrifigation or by filtration, dissolved in concentrated ammonia solution, and refluxed for 15–30 min. The complex was precipitated as the PF$_6$ salt, and the counterion was exchanged to chloride on a Sephadex QAE-A25 anion exchange column and finally purified on a Sephadex SP-C25 cation exchange column by elution with 0.05 M MgCl$_2$ in MeCN/water, 1:1. The fractions containing the complex were identified by TLC, combined, concentrated, and precipitated as colorless crystals by the addition of NH$_4$PF$_6$. Yield: 53%.

$^1$H NMR (acetone-d$_6$ 300 MHZ): δ 9.93 (2H, d), 9.42 (2H, d), 8.99 (2H. d), 8.64 (4H, m), 8.51 (2H, d), 8.32 (2H, d), 7.87 (2H, dd), 5.18 (6H, broad s). $^{13}$C NMR (acetone-d$_6$, 75.44 MHZ): δ 154.1, 153.6, 147.6 q, 146.6 q, 142.9, 141.5, 133.2 q, 129.2, 129.1, 128.3, 127.7. MS (electrospray): 645 (35, M$^+$-2PF$_6$), 495 (100, M$^+$-3PF$_6$); UV/vis (MeCN/water, 1:1, $1.905 \times 10^{-5}$ M): 302 (12 400), 271 (51 500), 222 (51 800); R$_f$=0.45 (silica gel, MeCN/water/n-butano/KNO$_3$, 4:1:1:0.1).

Enantiomer Separation. A 150 mg sample of the racemic mixture was separated under dark room conditions on a 150 cm long (d=3 cm) Sephadex CM-C25 ion exchange column eluting with 0.15 M (+)-potassium antimonyl tartrate in water (Keene, F. R., 1997, *Coord. Chem. Rev.* 166:121–159). The column was washed with deionized water and then carefully blown out onto a flat surface. The resin was divided into 20 equally sized pieces and eluted individually in the dark with MeCN/water, 1:1. The fractions containing metal complex were identified by TLC. The Δ and Λ enantiomers were separated by six fractions containing no product, with the Λ enantiomer eluting faster. The Λ enantiomer fractions were reduced in volume on a rotary evaporator and then diluted to 250 mL. The Δ enantiomer fractions were brought to a total volume of 250 mL, and the concentration was determined in both cases by absorption spectroscopy. The Δε values obtained for the Λ enantiomer are approximately 15% less than for the Δ sample, revealing that heating during rotary evaporation caused partial racemization.

Δ-[Rh(phen)$_2$(NH$_3$)$_2$]Cl$_3$: CD (acetonitrile/water, 1:1, 1.93×10$^{-5}$ M): 225 (27) 266 (44), 280 (−80), 304 (−16).

Λ-[Rh(phen)$_2$(NH$_3$)$_2$]Cl$_3$: CD (acetonitrile/water, 1:1, 2.51×10$^{-5}$ M): 227 (−19), 266 (−40), 280 (70), 303 (14).

(B) [Rh(bpy)$_2$(NH$_3$)$_2$]Cl$_3$:

The complex was synthesized according to the same procedure as described above for rac-[Rh(phen)$_2$(NH$_3$)$_2$](PF$_6$)$_3$ with the exception that instead of precipitation as the PF$_6$ salt the compound was isolated by evaporation. Yield: 94%.

$^1$H NMR (acetone-d$_6$, 300 MHZ): δ 9.45 (2H, d), 9.05 (2H, d), 8.89 (2H, d), 8.79 (2H, td), 8.45 (2H, td), 8.30 (2H, td), 8.05 (2H, d), 7.74 (2H, td), 5.06 (6H, broad s). MS (electrospray): 449.0 (45, M$^+$-3Cl), 447.1 (100, M$^+$-3Cl-2H), 430.1 (45, M$^+$-3Cl—NH$_3$); R$_f$=0.04 (silica gel, MeCN/water/n-butanol/KNO$_3$, 4:1:1:0.1).

(C) [Rh(phen)$_2$(NH$_3$)$_4$]Cl$_3$. [Rh(phen)Cl$_4$](H$_3$O$^+$) was prepared as described in the literature (McKenzie, E. D., and Plowman, R. A., 1970, *J. Inorg Nucl. Chem.* 32:199–212; Broomhead, J. H., and Grumley, W., 1971, *Inorg. Chem.* 10:2002–2009). The chloride ligands were exchanged to triflate by overnight treatment in neat triflic acid (Dixon et al. 1990, supra). The brownish solution was carefully introduced in chilled diethyl ether. The beige precipitate was separated either by centrifugation or by filtration, dissolved in concentrated ammonia solution, and refluxed for 30 min. The solution was allowed to cool and was then evaporated to dryness.

$^1$H NMR (DMSO-d$_6$, 300 MHZ): δ9.24 (2H, d), 9.03 (2H, d), 8.39 (2H, s), 8.27 (2H, m), 5.05 (6H, broad s), 4.04 (6H, broad s). MS (electrospray): 350.1 (32, M$^+$-3Cl-H), 349.4 (100, M$^+$-3Cl-2H) 348.5 (70, M$^+$-3Cl-3H).

Example 2
Synthesis of Rhodium Intercalating Compounds (A) In a typical preparation, 50 mg of Rh(III) starting material was dissolved in 32 mL of MeCN/water, 3:1, 0.1 M in NaOH. To this mixture was added 1 equiv or more of 9,10-phenanthrenequinone (to produce non-hindered control DNA photocleaving compounds) or 5,6-chrysenequinone (to produce hindered intercalating compounds). During constant stirring, the reaction was allowed to progress for approximately 18 h at room temperature. After neutralization with dilute hydrochloric acid and addition of 500 mL of water, the reaction mixture was loaded onto a Sephadex SP-C25 ion exchange column equilibrated in 0.05 M MgCl$_2$. The product was purified by elution with a gradient of 0.05–0.5 M MgCl$_2$, and the orange product bands were collected. The fractions were concentrated on a Waters Sep-Pak 5g C$_{18}$ cartridge and washed with copious amounts of water. The metal complex was eluted from the cartridge with a minimum volume of 0.1% TFA in MeCN/water, 1:1, and lyophilized to dryness.

rac[Rh(phen)$_2$(phi)Cl$_3$.

This orange compound was prepared according to the outline above. Yield: 86%. The characterization data are in good agreement with date in the literature (Pyle, A. M., et al. 1990, *Inorg. Chem.* 29:4487–4495).

Δ-[Rh(phen)$_2$(phi)](PF$_6$)$_3$.

Sodium hydroxide (0.6 g) was dissolved in 100 mL of MeCN/water, 1:1, containing Δ-[Rh(phen)$_2$(NH$_3$)$_2$]Cl$_3$ (18.4 mg, 0.037 mmol). 9,10-Phenanthrenequinone (8 mg, 0.038 mmol) in 50 mL of acetonitrile was added and the mixture stirred at room temperature. Aliquots (400 μL) were removed at intervals and mixed with 100 μL of 1.16 M HCl in MeCN/water, 1:1. These samples were subsequently analyzed by HPLC. After 1 day, the reaction mixture was neutralized with diluted hydrochloric acid and the volume reduced to approximately 20 mL. The complex was precipitated with 1 g of NH$_4$PF$_6$ and collected on Celite. The residue was dissolved in a minimum of acetonitrile and evaporated to dryness. Yield: 26.1 mg (64%). The characterization data ($^1$H NMR, MS, CD, UV/vis) agree well with published data (Pyle, A. M., et al. 1990, *J. Am. Chem. Soc.* 112:9432–9434) with slightly higher Δε values observed by CD spectroscopy.

CE (acetonitrile, 1.47×10$^{-5}$ M): 261 (99), 275 (−179), 346 (−24).

rac-[Rh(bpy)$_2$(phi)](PF$_6$)$_3$.

This product was synthesized starting from [Rh(bpy)$_2$(NH$_3$)$_2$]$^{3+}$. The characterization data agree well with published data (Sitlani, A., and Barton, J. K., 1994, *Biochemistry* 33:12100–12108).

rac-[Rh(bpy)$_2$(chrysi)]Cl$_3$.

[Rh(bpy)$_2$(NH$_3$)$_2$](PF$_6$)$_3$ (195.5 mg, 0.22 mmol) and 5,6-chrysenequinone (56.8 mg, 0.22 mmol) were dissolved with rapid stirring in 15 mL of acetonitrile under atmospheric conditions. Aqueous sodium hydroxide (5 mL, 0.4 M) was added and the reaction vessel capped to prevent evaporation. After 3 h the reaction was stopped by the addition of 5–6 mL of 0.4 M hydrochloric acid. The mixture was diluted, purified, and isolated as described above. Yield: 28 mg (83%).

$^1$H NMR (MeOH-d$_4$, 500 MHZ): δ 8.94 (2H, t), 8.86 (2H, t), 8.80 (1H, d), 8.77 (1H, d), 8.56 (2H, split t), 8.44 (5H, m), 8.40 (1H, d), 8.15 (1H, m), 8.03 (1H, m), 7.95 (3H,m), 7.86 (1H, d), 7.81 (1H, d), 7.64 (5H, m). $^{13}$C NMR (MeOH-d$_4$, 125.73 MHZ): δ 183.3, 177.3, 175.4, 157.4, 157.2, 157.2, 153.8, 153.2, 152.1, 144.6, 144.5, 143.9, 143.8, 139.7, 138.8, 138.4, 136.2, 135.7, 132.3, 132.2, 132.0, 131.8, 130.9, 130.77, 130.6, 130.2, 129.4, 127.7, 127.6, 127.3, 126.9, 126.8, 123.9, 122.9, 120.8, 118.6, 116.3, 114.1. MS (FAB): 671 (24% M$^+$-3Cl), 670.1 (63, M$^+$-3Cl-H), 669.1 (100, M$^+$-3Cl-2H); UV/vis (water, 7.76×10$^{-6}$ M): 303 (57 000), 315 (52 200), 391 (10 600). ε$_{271\,nm}$: 63 800 M$^{-1}$ cm$^{-1}$ (pH isosbestic point); R$_f$=0.33 (silica gel, MeCN/water/n-butanol/KNO$_3$, 4:1:1:0.1).

(B) Enantiomeric Separation.

The enantiomers of the complex were separated on a Sephadex SP-C25 column eluted with 0.15 M of (+)- KSb tartrate in water (Keene, 1997, supra) The separated orange fractions, with the Λ enantiomer being eluted faster, were collected and concentrated on a Waters Sep-Pak 5 g C$_{18}$ cartridge. After washing with water, the residue was dissolved in a minimum of MeCN/water, 1:1, and evaporated to dryness.

Δ-[Rh(bpy)$_2$(chrysi)]Cl$_3$: CD (water, 7.76×10$^{-6}$ M): 233 (34) 264 (26), 286 (−12), 308 (−42), 318 (−100), 341 (6).

Λ-[Rh(bpy)$_2$(chrysi)]Cl$_3$: CD (water, 7.76×10$^{-\neq}$M): 233 (−34) 264 (−26), 286 (12), 308 (42), 318 (100), 341 (−6).

rac-[Rh(d$_8$-bpy)$_2$(chrysi)]Cl$_3$: This complex was synthesized as above but with deuterated 2,2'-bipyridine.

rac-[Rh(phen)$_2$(chrysi)]Cl$_3$: This compound was prepared analogously to rac-[Rh(bpy)$_2$(chrysi)]Cl$_3$. Yield: 77%.

rac-[Rh(phen)(phi)$_2$]Cl$_3$: This orange compound was prepared from [Rh(phen)(NH$_3$)$_4$]Cl$_3$ with 2 equiv of 9,10-phenanthrenequinone following the outline above. The product was purified on a Sephadex SP-C25 cation exchange column eluting with 1.0 M MgCl$_2$ acidified with a few drops of diluted HCl. Yield: 54%. The characterization data are in good agreement with the literature (Sitlani, 1994, supra).

rac-[Rh(phen)(chrysi)$_2$]Cl$_3$: This orange/brown compound was prepared from [(Rh(phen)(NH$_3$)$_4$]Cl$_3$ with 5 eq of chrysene quinone as described above, and purified using the method described for [Rh(phen)(phi)$_2$]Cl$_3$. Yield: 48%.

rac-[Rh(phen)(phi)(chrysi)]Cl$_3$: [Rh(phen)(NH$_3$)$_4$](CF$_3$SO$_3$)$_3$ (17 mg, 0.021 mmol) was combined with 9,10- phenanthrenequinone (5.4 mg, 0.026 mmol) in acetonitrile (9.6 mL), water (2.0 mL), and NaOH solution (1.6 M, 1.2 mL). After 60 min of stirring at ambient temperature, 5,6-chrysenequinone (9.9 mg, 0.039 mmol) was added. The reaction was stopped after 20 h by neutralization with diluted hydrochloric acid. The product was purified on a Sephadex SP-C25 cation exchange column eluting with a gradient of 0.05–0.5 M $MgCl_2$. The red product band was collected, and the fractions were concentrated on a Waters Sep-Pak, 5 g $C_{18}$ cartridge and washed with copious amounts of water. The metal complex was eluted from the cartridge with a minimum volume of 0.1% TFA in MeCN/water, 1:1, and lyophilized to dryness. Yield: 14 mg (75%).

$^1$H NMR ($D_2O$, 300 MHZ): complicated multiplets centered at 8.94, 8.36, 8.08, 7.80, and 7.60. Integrals were consistent with the desired product.

MS (electrospray): 745.3 (18, $M^+$-3Cl), 744.3 (75, $M^+$-3Cl-1H), 743.2 (100, $M^-$-3Cl-2H).

Example 3

Photocleavage

A set of DNA duplexes was prepared having the following sequence:

3'-GTGTACGTXCTGAGGCG-5'(SEQ ID NO:1)

5'-CACATGCAYGACTCCGC-3'(SEQ ID NO:2), where X and Y were varied to provide A-T, G-C, and the following mismatches: C-C, C-A, T-T, A-A, T-C, T-G, G-A, and G-G. All oligonucleotides were prepared using standard phosphoramidite chemistry, and were purified by reverse phase HPLC. The oligonucleotides were 5' end-labeled with γ-$^{32}$P ATP (Dupont-NEN) and T4 polynucleotide kinase (New England Biolabs).

Duplexes (10 μM) were incubated with Δ or Λ [Rh(bpy)$_2$(chrysi)]$^{3+}$(1 μM in 50 mM Tris, 20 mM NaOAc, 18 mM NaCl, pH 7.0) for 11 minutes, then irradiated for 13 min at 365 nm using an Oriel HgXe arc lamp. The products were analyzed by PAGE (20%, denaturing), imaged using a Molecular Dynamics Phosphorimager. The results are shown in FIG. 1. The lanes labeled A+G and C+T are standard Maxam-Gilbert sequencing reactions: the remaining columns show cleavage (or lack of cleavage) for each tested mismatch with each enantiomer. The strongest cleavage intensity was observed with the Δ enantiomer on the duplex containing the C-C mismatch. Here, cleavage occurred to the 3' side of the mismatch site. Similar, although less intense cleavage was observed at the other pyrimidine-pyrimidine mismatches T-T and T-C. C-A, the single purine-pyrimidine mismatch that is cleaved, showed a different pattern. Strong cutting is evident at the mismatched C and neighboring the base 3' to the mismatch site.

Unlike the other recognized mismatches, the cleavage 3' to C-A results in two products having different gel mobility, possibly the result of chemically different polymer termini. The cleavage of A-A was also distinctive. The Δ enantiomer promotes strong cleavage at the base 3' to the site, and a small amount of cleavage at the A-A site itself The A-A mismatch is the only pair cleaved by the Λ enantiomer, with weaker cleavage than the Δ enantiomer.

Other DNA photocleavage experiments on similar systems showed DNA cleavage by Δ[Rh(bpy)$_2$(chrysi)]$^{3+}$ is affected by the bases to the 5' and 3' side of the mismatch site (T/A in SEQ ID NO:1 and C/G in SEQ ID NO:4). When these bases were systematically changed, photocleavage was observed at 83 of 104 of the mismatch-sequence context combinations (80%).

Example 4

Photocleavage Titration

Figure 2:
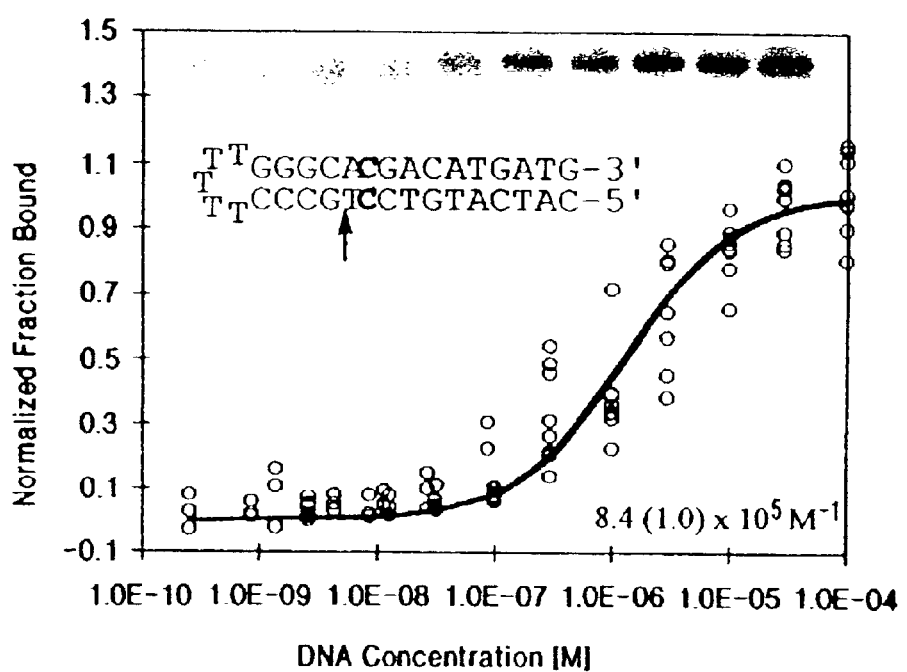
FIG. 2 shows the results of photocleavage as a function of DNA concentration

A hairpin DNA oligonucleotide was synthesized with the sequence:

5'-CATCATGTCCTGCCCTTTTTGGGCACGACAT GATG-3' (SEQ ID NO:3), having a single C-C mismatch. The hairpin was photocleaved as described in Example 2 above with Δ[Rh(bpy)2(chrysi)]$^{3+}$ at either 313 nm or 365 nm for 7.5 to 15 min. Hairpin DNA concentration was varied from 3×10$^{-10}$ M to 1×10$^{-4}$ M, with the Rh complex used at 0.10× the DNA concentration. The cleavage products were eluted through 20% denaturing polyacrylamide gels, and analyzed using a Molecular Dynamics Phosphorimager and ImageQuant software. The results are shown in FIG. 2. Cleavage was observed 3' to the C-C mismatch on both sides of the hairpin: only the cleavage band closest to the end label was quantitated. Data from multiple trials was normalized (open circles) and fit to a standard single binding site binding model (solid line).

The thermodynamic binding constant was determined to be 8.4 (±1.0)×10$^5$ M$^{-1}$. Similar DNA photocleavage titrations at other mismatch sites have measured the affinity of Δ [Rh(bpy)2(chrysi)]$^{3+}$ between 1×10$^7$ and 3×10$^5$ M$^{-1}$. To examine the level of selectivity the average binding constant of Δ[Rh(bpy)$_2$(chrysi)]$^{3+}$ to B-form DNA was also determined. Photocleavage on a 33mer correctly matched hairpin and competitive titration with unlabeled 25mer B-DNA yielded a value of 4 (±2)×10$^4$ M$^{-1}$ for the average non-specific binding affinity.

Although the invention has been described with reference to the presently preferred embodiment, it should be understood that various modifications can be made without departing from the spirit of the invention. Accordingly, the invention is limited only by the following claims.

What is claimed is:

1. A composition for treating a condition wherein the condition includes error or damage in a duplex polynucleotide, comprising:

an effective amount of a composition e comprising an active hindered intercalating compound, wherein the compound comprises a compound of the formula:

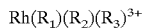

wherein $R_1$ and $R_2$ are each independently aryl, heteroaryl, substituted aryl or substituted heteroaryl of 1 to 5 rings and $R_3$ is a group of the formula

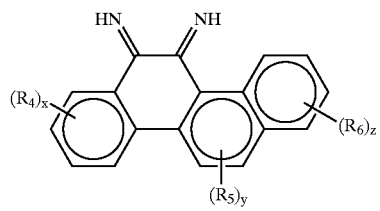

where x and z are each independently an integer from 1 to 4 and y is an integer from 1 to 2, and $R_4$, $R_5$, and $R_6$ are each independently H—, halo, HO—, $H_2N$—, CN—, $O_2N$—, HS—, $O_3S$—, $O_3SO$—, —COOH, —$CONH_2$, R, RO—, RNH—, $R_a$, $R_bN$—, $RO_3S$—, $RO_3SO$—, —COOR, —CONHR, or —$CONR_aR_b$, where R, $R_2$ and $R_b$ are each independently lower alkyl, cycloalkyl, lower alkenyl, lower alkynyl, or phenyl, or two $R_4$, $R_5$, or $R_6$ together form a fused aryl ring and a pharmaceutically acceptable excipient.

2. The composition of claim 1, wherein said compound catalyzes photocleavage of DNA having damage or errors.

3. The composition of claim 1, wherein said compound is $Rh(bpy)_2(chrysi)^{3+}$ or $Rh(phen)_2(chrysi)^{3+}$.

4. The composition of claim 3, wherein said compound comprises $\Delta Rh(bpy)_2(chrysi)^{3+}$.

5. The composition of claim 1, wherein the error is a base pair mismatch.

* * * * *